(12) United States Patent
Ohta et al.

(10) Patent No.: US 7,157,459 B2
(45) Date of Patent: Jan. 2, 2007

(54) POSTOPERATIVE ADJUVANT CHEMOTHERAPY WITH UFT

(75) Inventors: Mitsuo Ohta, Fukoka (JP); Hiromi Wada, Shiga (JP); Harubumi Kato, Tokyo (JP); Yukito Ichinose, Fukuoka (JP); Masahiro Tsuboi, Tokyo (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 11/115,394

(22) Filed: Apr. 27, 2005

(65) Prior Publication Data

US 2005/0245478 A1    Nov. 3, 2005

Related U.S. Application Data

(60) Provisional application No. 60/565,870, filed on Apr. 28, 2004.

(51) Int. Cl.
*A01N 43/58* (2006.01)
(52) U.S. Cl. ....................... 514/247; 514/183
(58) Field of Classification Search ................ 514/269
See application file for complete search history.

(56) References Cited

U.S. PATENT DOCUMENTS 6,303,583 B1 * 10/2001 Kusunoki .................... 514/50

OTHER PUBLICATIONS

Fujii, S., et al., "Effect of coadministration of uracil or cytosine on the anti-tumor activity of clinical doses of 1-(2-tertahydrofuryl)-5-fluorouracil and level of 5-fluorouracil in rodents" *Gann* 70:209-14, 1979.
Ikenaka, K., et al., Effect of uracil on metabolism of 5-fluorouracil in vitro, @ *Gann* 70:353-9, 1979.
Ho, D.H., et al., "Comparison of 5-fluorouracil pharmacokinetics in patients receiving continuous 5-flourouracil infusion and oral uracil plus N1-(2'Tertahydrofuryl)-5-flourouracil", *Clin. Cancer Res.* 4:2085-8, 1998.
Shimizu, E., et al., "A phase II study of UFT in non-small cell lug cancer", *Jpn. J. Cancer Chemother*. 13:2970-3, 1986.
Keicho, N., et al., "Phase II study of UFT in patients with advanced non-small cell lung cancer," *Jpn. J. Clin. Oncol*. 16:143-6, 1986.
Ichinose, Y., et al., A phase II trial of oral UFT and cisplatin in inoperable non-small cell lung cancer, *Cancer* 75:2677-80, 1995.
Ichinose, Y., et al., "UFT plus cisplatin combination chemotherapy in the treatment of patients with advanced nonsmall cell lung carcinoma," *Cancer* 88:318-23, 2000.
Saito, J., et al., "A phase II trial of oral UFT plus cisplation (CDDP) in patients with non-small cell lung cancer (NSCLC)," *Lung Cancer* 31:285-93, 2001.
Ichinose, Y., et al., "UFT plus cisplatin with concurrent radiotherapy for locally advanced non-small-cell long cancer: a multiinstitutional phase II trial," *Prog. Proc. Am. Soc. Clin. Oncol*. 21:321a (Abstract), 2002.

Ichinose, Y., et al., "A phase II trial UFT plus cisplatin with concurrent radiotherapy for locally advanced non-small-cell lung cancer," *Oncology* 13(3):98-101, 1999.
Schiller, J.H., et al., "Comparison of four chemotherapy regimens for advanced non-small cell lung cancer," *N. Engl. J. Med*. 346:92-8, 2002.
Vokes, E.E., et al., "Randomized phase II study of cisplatin with gemcitabine or paclitaxel or vinorelbine as induction chemotherapy followed by concomitant chemoradiotherapy for stage IIIB non-small-cell lung cancer: cancer and leukemia group B study 9431," *J. Clin. Oncol*. 20:4191-8, 2002.
Wada, H., et al., Adjuvant chemotherapy after complete resection in non-small-cell lung cancer, *J. Clin. Oncol*. 14:1048-54, 1996.
Okimoto, N., et al., "A randomized controlled postoperative adjuvant chemotherapy trial of CDDP+VDS+UFT and UFT alone in comparison with operation only for non-small cell lung carcinomas (Second Study);" *Jpn. J. Lung Cancer* 36:863-71, 1996.
Mountain, C.F., A new international staging system for lung cancer, *Chest*. 89(4):225s-33s, 1986.
*WHO Handbook for Reporting Results for Cancer Treatment*, Geneva: World Health Organization Offset Publication No. 48, 14-21, 1979.
Shirakusa, T., et al., "Lung cancer in Japan: Analysis of lung cancer registry for resected cases in 1994," *Jpn. J. Lung Cancer* 42:555-66, 2002.
Breathnach, O.S., et al., "Bronchioloalveolar carcinoma of the lung: recurrences and survival in patients with stage I disease," *J. Thorac. Cardiovasc. Surg*. 121:42-7, 2001.
Myrdal, G., et al., "Survival in primary lung cancer potentially cured by operation: influence of tumor stage and clinical characteristics," *Ann. Thorac. Surg*. 75:356-63, 2003.
Noguchi, M., et al., "Small adenocarcinoma of the lung: histologic characteristics and prognosis," *Cancer* 75:2844-52, 1995.
Kodama, K., et al., "Prognostic value of ground-glass opacity found in small lung adenocarcinoma on high-resolution CT scanning," *Lung Cancer* 33:17-25, 2001.
Tanaka, F., et al., "Apoptosis and p53 status predict the efficacy of postoperative administration of UFT in non-small cell lung cancer," *Br. J. Cancer* 84:263-9, 2001.
Feld, R., et al., "Adjuvant chemotherapy with cyclophosphamide, doxorubicin, and cisplatin in patients with completely resected stage I non-small-cell lung cancer," *J. Natl. Cancer Inst*. 85:299-306, 1993.
Ohta, M., et al., "Adjuvant chemotherapy for completely resected stage III non-small-cell lung cancer," *J. Thorac. Cardiovasc. Surg*. 106:703-8, 1993.

(Continued)

*Primary Examiner*—Ardin H. Marschel
*Assistant Examiner*—Michel Graffeo
(74) *Attorney, Agent, or Firm*—Rothwell, Figg, Ernst & Manbeck, P.C.

(57) ABSTRACT

The present invention provides an improved method for treating lung cancer, preferably non-small cell lung cancer, by orally administering UFT to postoperative lung cancer patients.

4 Claims, 4 Drawing Sheets

OTHER PUBLICATIONS

Ichinose, Y., et al., "A Randomized Phase III Trial of Postoperative Adjuvant Chemotherapy in Patients with Completely Resected Stage IIIa-N2 Non-Small Cell Lung Cancer: Japan Clinical Oncology Group (JCOG9304) Trial," *Prog. Proc. Am. Soc. Clin. Oncol.* 20:311a (Abstract), 2001.

Scagliotti, G.V., et al., "Randomized study of adjuvant chemotherapy for completely resected stage I, II, or IIIA non-small-cell lung cancer," *J. Natl. Cancer Inst.* 95:1453-1461, 2003.

Tanaka, F., et al., "Postoperative oral administration of UFT for completely resected pathologic stage I non-small cell lung cancer: the West Japan Study Group for Lung Cancer Surgery (WJSG), the 4th Study," *Prog. Proc. Eur. Cancer Conference* 37:S29 (Abstract), 2001.

Tada, H., et al., "Randomized Study of Adjuvant Chemotherapy for Completely Resected Non-Small Cell Lung Cancer," *Prog. Proc. Am. Soc. Clin. Oncol.* 21:313a (Abstract), 2002.

Endo, C., et al., "A randomized trial of postoperative UFT therapy in p stage I, II non-small cell lung cancer: North-East Japan Study Group for Lung-Cancer Surgery," *Lung Cancer* 40:181-6, 2003.

Imaizumi, M., et al., "A randomized trial of postoperative adjuvat chemotherapy for p-stage I non-small cell lung cancer (4th cooperative study)," *Prog. Proc. World Conference* 41:S54 (Abstract), 2003.

Yonekura, K., et al., "UFT and its metabolites inhibit the angiogenesis induced by murine renal cell carcinoma, as determined by a dorsal air sac assay in mice," *Clin. Cancer Res.* 5:2185-91, 1999.

Hamada, C., et al., "Efficacy or oral UFT for adjuvant chemotherapy after complete resection of non-small cell lung cancer: Meta-analysis of six randomized trials in 2003 patients," *Prog. Proc. Euro. Cancer Conference* 39:S231 (Abstract), 2003.

Mountain, C.F., "Revisions in the International System for Staging Lung Cancer," *Chest* 111(6):1710-17, 1997.

Mountain, C.F., et al., "Regional Lymph Node Classification for Lung Cancer Staging," *Chest* 111(6):1718-1723, 1997.

Schoenfeld, D.A., et al., "Nomograms for calculating the number of patients needed for a clinical trial with survival as an endpoint," *Biometrics* 38:163-170, 1982.

Haybittle, J.L., "Repeated assessment of results in clinical trials of cancer treatment," *Br. J. Radiol.* 44:793-797, 1971.

Kato, H., et al., "A randomized phase III trial of adjuvant chemotherapy with UFT for completely resected pathological stage I (T1N0M0, T2N0M0) adenocarcinoma of the lung," *Proc. Am. Soc. Clin. Oncol.* 22:621, 2003 (Abstract 2498).

\* cited by examiner

POSTOPERATIVE ADJUVANT CHEMOTHERAPY WITH UFT

This Application claims the benefit of U.S. Provisional Application No. 60/565,870, filed Apr. 28, 2004.

FIELD OF THE INVENTION

The present invention relates to postoperative treatment of cancer using UFT. In particular, the invention relates to improved methods for treating lung cancer by postoperative adjuvant chemotherapy with UFT.

BACKGROUND OF THE INVENTION

UFT is an oral anticancer agent comprised of tegafur and uracil at a molar ratio of 1 to 4 which has good absorption in the small intestine. (Fujii, S., et al., 1979; U.S. Pat. No. 4,328,229). Tegafur is gradually converted to 5-fluorouracil via the metabolism of liver enzyme P450. Uracil enhances the serum 5-fluorouracil concentration by the competitive inhibition of dihydropyrimidine dehydrogenase, the enzyme responsible for 5-fluorouracil catabolism. (Ikenaka, K., et al., 1979). Oral UFT administration reportedly generates a higher maximum plasma level of 5-fluorouracil than the protracted intravenous injection of 5-flourouracil given in a dose equimolar to the tegafur in UFT. (Ho, D. H., et al., 1998).

The response rate of single UFT treatments in patients with advanced stage lung cancer is reported to be 6 to 8 percent. (Shimizu, E., et al., 1986; Keicho, N., et al., 1986). Combination chemotherapy consisting of a daily administration of UFT for two or three weeks, and a bolus injection of cisplatin in advanced non-small cell lung cancer patients yields a response rate of 29 percent to 38 percent and a median survival time of eight to thirteen months. (Ichonose, Y., et al., 1995; Ichinose, Y., et al., 2000; Saito, J., et al., 2001). In two trials for locally advanced non-small cell lung cancer patients, the combination chemotherapy of UFT plus cisplatin with concurrent radiotherapy shows a response rate of 80 percent (Ichinose, Y., et al., 2002) and 94 percent (Ichinose, Y., et al., 1999) and a median survival rate of 16.5 months. (Ichinose, Y., et al., 2002). These results of UFT plus cisplatin chemotherapy regimens are comparable to those of other recently published cisplatin based doublet chemotherapy regimens. (Schiller, J. H., et al., 2002; Vokes, E. E., et al., 2002).

Adenocarcinoma, a form of non-small cell lung cancer (NSCLC), accounts for approximately 40% of all cases of lung cancer. It is the most common form of NSCLC and the most common type of lung cancer overall.

Concerning adjuvant treatment using UFT, the West Japan Study Group for Lung Cancer Surgery reported that postoperative adjuvant treatment with UFT (400 mg/day for 1 year) in patients with completely resected stage I-III disease prolonged survival significantly longer than observation alone. (Wada, H., et al., 1996). The 5-year survival rate was 64 percent in the UFT group and 49 percent in the control group (P=0.02). In a subgroup analysis, no statistically significant difference in the overall survival of patients with squamous cell carcinoma between the two groups was observed (P=0.24). In contrast, for the patients with adenocarcinoma in the UFT group, most of whom had stage I disease, survival was significantly better than for those in the control group (P=0.009). (Okimoto, N., et al., 1996).

Improved methods for extending survival while causing minimal side effects in postoperative lung cancer patients, particularly in patients with adenocarcinoma, are needed.

SUMMARY OF THE INVENTION

In one aspect, the present invention relates to a significantly improved method for treating lung cancer, preferably non-small cell lung cancer, and more preferably adenocarcinoma, by postoperative adjuvant chemotherapy with UFT orally administered substantially daily to a postoperative lung cancer patient. In a preferred method, about 100–500 mg/m$^2$/day of UFT, preferably about 200–300 mg/m$^2$/day of UFT, and most preferably an average of about 250 mg/m$^2$/day UFT is orally administered to a postoperative lung cancer patient in need thereof for a period of at least about two years.

In a preferred embodiment, the present invention relates to treating a patient having pathological stage I, and more preferably pathological stage IB, adenocarcinoma of the lung.

In a more preferred embodiment, the present invention relates to treating adenocarcinoma which has been completely resected prior to treatment.

In another preferred embodiment, the present invention relates to treating a patient having a primary tumor of a size more than 2 cm, and preferably about 2 to 3 cm, or more, and more preferably wherein the primary tumor is classified as T2 according to the TNM classification (See Mountain, C. F., 1997; Mountain, C. F., et al., 1997).

DETAILED DESCRIPTION OF THE INVENTION

Figure 1A:
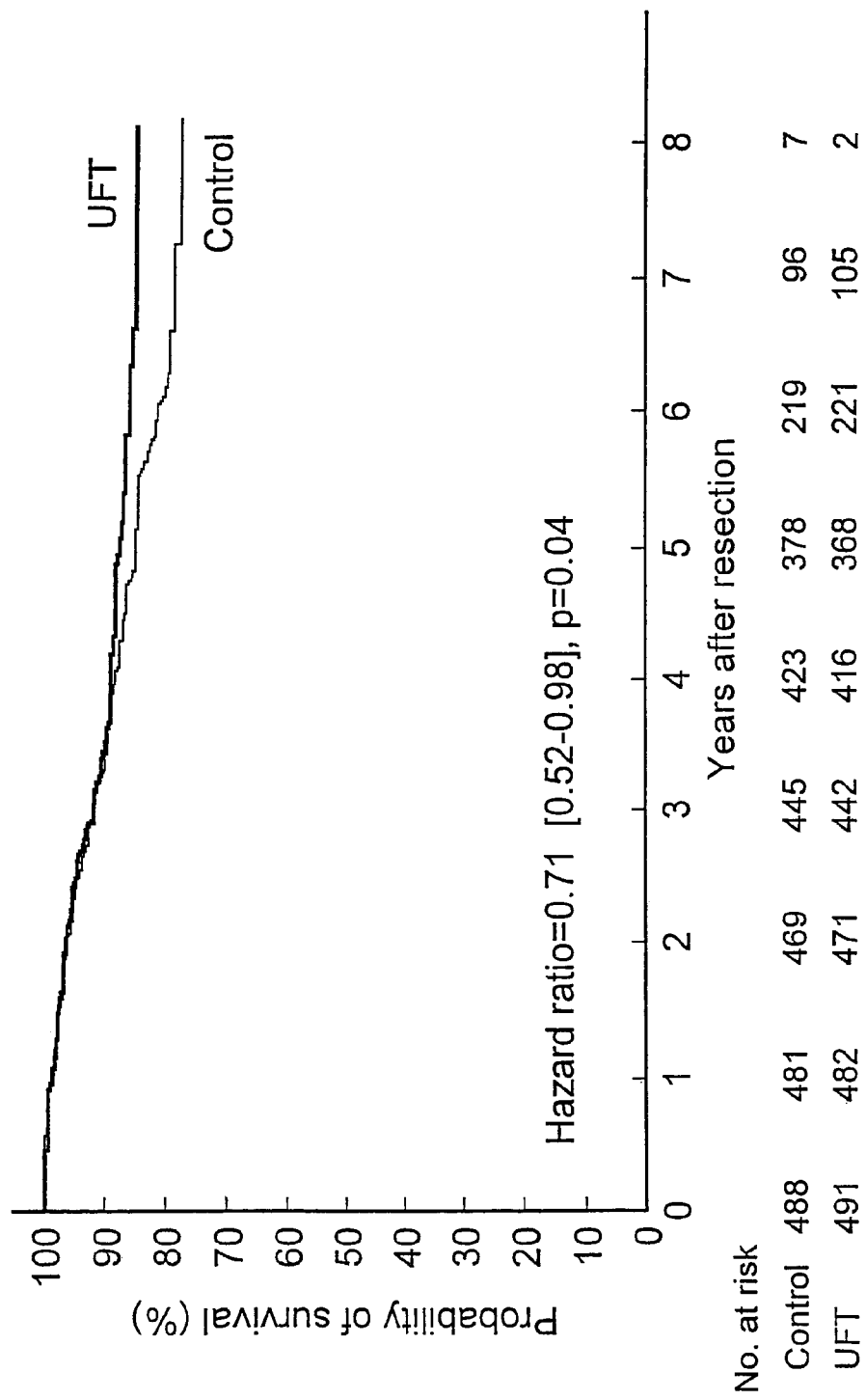
FIG. 1 shows the survival of all eligible 979 patients (Panel A), 263 patients with T2 Disease (Panel B) and 716 patients with T1 disease (Panel C) assigned to the UFT group and the control group. Error bars represent the 95 percent confidence intervals. The P value was calculated using the stratified logrank test.

In accordance with the invention, the oral administration of UFT (a combination of tegafur and uracil at a ratio of 1:4) as adjuvant chemotherapy was shown to prolong the survival of patients with resected adenocarcinoma, among whom most patients had pathological stage I disease. In particular, postoperative adjuvant chemotherapy using UFT (250 mg/m$^2$/day) for a period of 2 years was found to yield a significant improvement in the survival of patients with pathological stage I adenocarcinoma of the lung, especially in stage 1B (T2NOMO) (Kato, H., et al., 2003).

Patients with completely resected pathological stage I adenocarcinoma of the lung were randomized with stratification according to their pathological T status (T1 versus T2), gender and age to either receive the oral administration of UFT (tegafur 250 mg/m$^2$/day) for two years or no treatment. The primary endpoint was overall survival.

Patient Characteristics

Between January 1994 and March 1997, 999 patients were enrolled in the trial and 501 patients and 498 patients were randomly assigned to receive either no treatment or UFT, respectively. However, seven patients in the UFT group and 13 patients in the control group were found to be ineligible for the following reasons: pathological N1 or M1 disease in seven patients, a histology other than adenocarcinoma in six, no laboratory data at registration in two and other miscellaneous reasons in five. Therefore, the number of all eligible patients was 488 in the control group and 491 in the UFT group. The clinical characteristics of those eligible patients are listed in Table 1. There were no statistically significant differences in the base line characteristics of the patients. All but one patient in each group underwent lobectomy.

Adverse Reactions and Compliance

Of the 498 patients randomized to the UFT group, 482 patients received an oral administration of UFT. Table 2 lists the incidence of UFT-related adverse reactions. Few severe adverse reactions were associated with UFT administration. There was no grade 4 adverse reaction. In total, 10 (2 percent) of 482 patients developed a grade 3 adverse reaction.

The percentage of compliance for UFT administration was calculated based on the number of patients who actually took UFT and the number of patients without recurrence, second cancer or death who were expected to take UFT. The percentage of compliance was 80 percent (95 percent confidence interval: 77 to 84 percent) at 6 months, 74 percent (95 percent confidence interval: 70 to 78 percent) at 12 months, 69 percent (95 percent confidence interval: 65 to 73 percent) at 18 months and 61 percent (95 percent confidence interval: 77 to 84 percent) at 24 months. The main reasons for a discontinuation of UFT administration were as follows: an adverse reaction in 123 patients, patient refusal in 52 and the doctor's judgment in 34.

Overall Survival

The median follow-up for the surviving patients was 72 months in the UFT group and 73 months in the control group. The numbers of censored patients were 361 in the UFT group and 359 in the control group. At the last follow-up, 65 patients in the UFT group and 89 in the control group had died and the overall survival showed a statistically significant difference based on the stratified logrank test as shown in FIG. 1A. The 5-year survival rate was 88 percent (95 percent confidence interval: 85 to 91 percent) in the UFT group and 85 percent (95 percent confidence interval: 82 to 89 percent) in the control group. When the survival analysis was performed in all 999 randomized patients, the result did not change and the p-value of the difference between the two groups was 0.047.

The predetermined covariates were age (<65 years versus >65 years), sex (male versus female), performances status (0 versus 1 plus 2), T status (T1 versus T2) and treatment groups. The covariates were selected according to multivariate analysis using a stepwise procedure under the condition that the p value was less than 0.05. The selected covariates were as follows: age (hazard ratio=2.02, 95 percent confidence interval=1.46 to 2.80 percent; P<0.001), T status (hazard ratio=1.95, 95 percent confidence interval=1.41 to 2.69 percent; P<0.001) and sex (hazard ratio=0.66, 95 percent confidence interval=0.48 to 0.91 percent; P=0.01) and treatment groups (hazard ratio=0.72, 95 percent confidence interval=0.53 to 1.00 percent; P=0.05).

Figure 2:
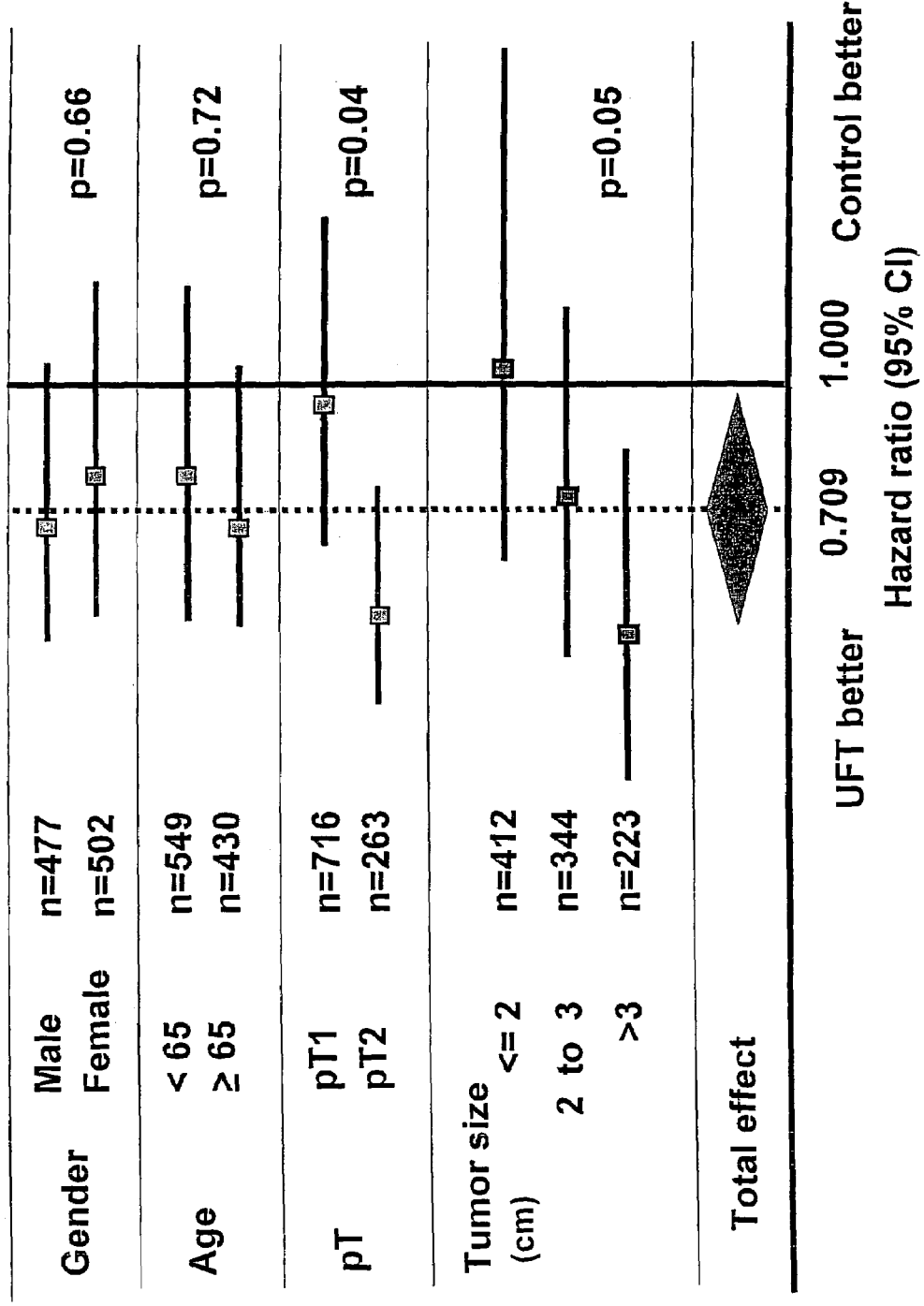
FIG. 2 shows the interaction of prognostic factors with treatment in survival. Each square estimates the treatment effect, and horizontal lines represent the 95 percent confidence intervals. The diamond corresponds to the 95 percent confidence intervals for whole subjects. P-value of the tumor size is for the interaction with two groups of <=2 and >3 cm.

An interaction between four prognostic factors listed in FIG. 2 and the treatment was then evaluated. Since the T status is mainly classified by the minimum diameter of the primary tumor, the tumor size was added to the analysis. As shown in FIG. 2, significant interaction of either T status or the tumor size with the treatment was observed.

Figure 1B:
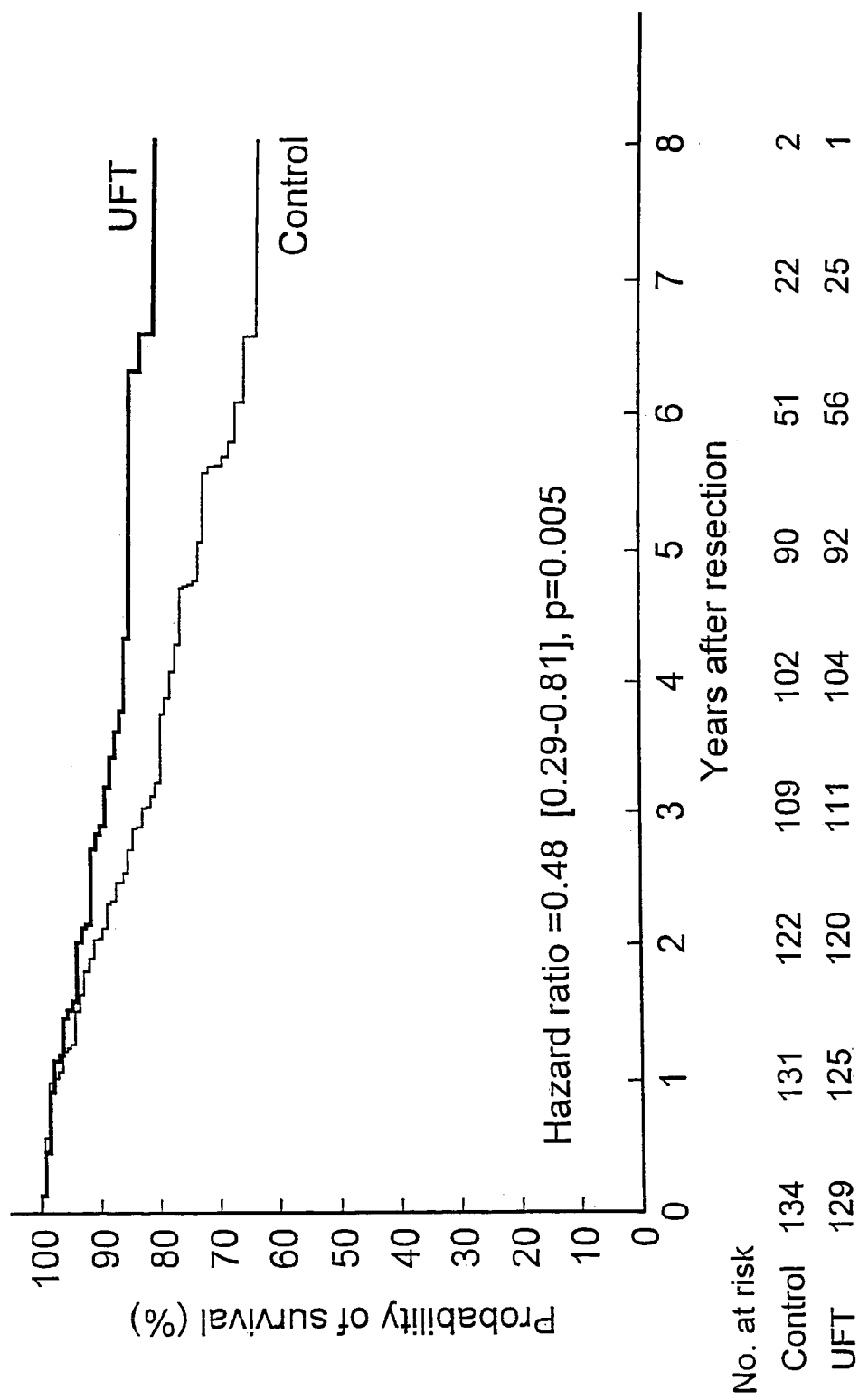
Figure 1C:
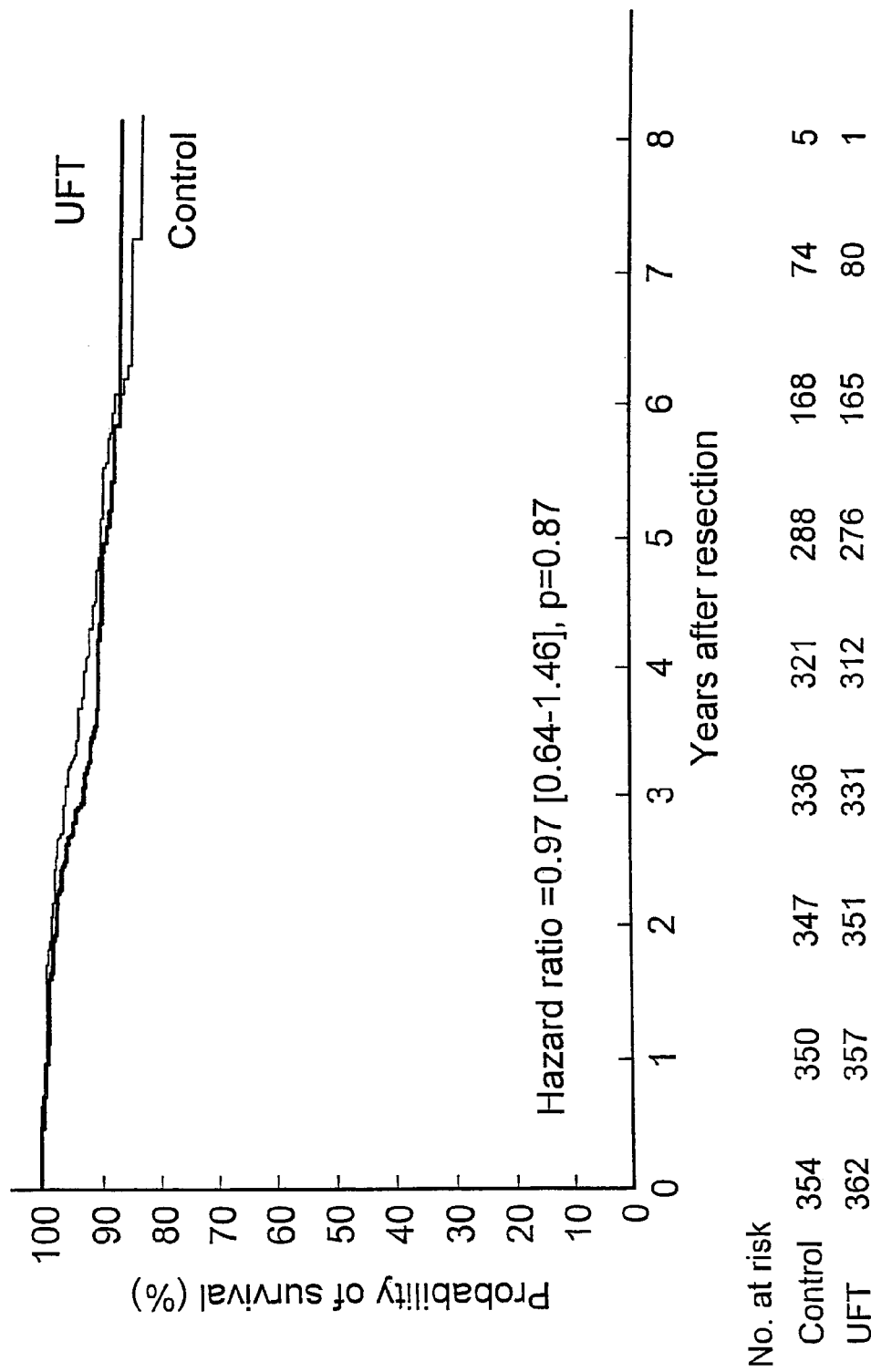

The patients with T2 disease in the UFT group had a significantly better survival than those in the control group while there was no survival difference between the UFT and the control group in the patients with T1 disease. The 5-year survival rate of patients with T2 disease was 85 percent (95 percent confidence interval: 79 to 91 percent) in the UFT group and 74 percent (95 percent confidence interval: 68 to 81 percent) in the control group (FIG. 1B). The overall survival between the two groups was statistically significantly different (P=0.005 by the logrank test). The 5-year survival rate of patients with T1 disease was 89 percent in the UFT and 90 percent in the control groups (FIG. 1C). The 5-year survival rate of patients with tumor size of <=2 cm, 2 to 3 and >3 was 89, 89 and 85 percent in the UFT group and 91, 86 and 74 percent in the control group, respectively.

Pattern of Failure and Cancer-Free Survival

As shown in Table 3, either recurrence or a second primary cancer as the first treatment failure after operation was documented in 23 percent of the patients in the UFT group and in 26 percent of those in the control group. Among 716 patients with T1 disease, either recurrence or a secondary primary cancer as the first treatment failure was observed in 69 patients (19 percent) in the UFT group and 76 patients (22 percent) in the control group while it was observed in 42 patients (33 percent) in the UFT group and 53 patients (40 percent) in the control group among 263 patients with T2 disease. The cancer-free survival between the UFT and the control group was not statistically significantly different based on a Kaplan-Meier analysis (P=0.25 by the stratified logrank test). The survival of patients after the diagnosis of either recurrence or second primary cancer did not differ significantly between the groups (P=0.14 by the logrank test): the 1- and 2-year survival rates after diagnosis were 65 percent and 50 percent in the UFT group and 65 percent and 42 percent in the control group, respectively.

The Japanese Association for Chest Surgery and Japan Lung Cancer Society recently reported on the long-term survival rate of 7,408 lung cancer patients who underwent a surgical resection in 1994 when the present trial started. (Shirakusa, T., et al., 2002). The main histologies were adenocarcinoma (56 percent) and squamous cell carcinoma (33 percent). The 5-year survival rate of patients with pathological T1N0M0 and T2N0M0 was 79 percent and 60 percent, respectively. In the present study focusing on the histology of adenocarcinoma, the 5-year survival rate in the control group was 90 percent in patients with T1N0M0 and 74 percent in those with T2N0M0. Although the latter figures could not be directly compared with the former due to different histologic patterns and the times that the data were collected, the 5-year survival of the control patients in the present study is thought to be at least one of the best results reported. (Breathnach, O. S., et al., 2001; Myrdal, G., et al., 2003). Those findings may indicate the quality of the operation and the accuracy of surgical staging in the study group.

It was thus shown that postoperative adjuvant chemotherapy with UFT has a beneficial effect on the survival of resected patients with stage I adenocarcinoma, although little or no benefit was observed in the patients with T1N0 disease. Recently, the number of patients with small sized adenocarcinoma has increased due to the increased use of CT. In fact, 412 (42 percent) of total 979 patients had adenocarcinoma measuring less than 2 cm in size. Such small sized adenocarcinomas often include bronchioloalveolar carcinoma which has little chance of recurrence after operation. (Noguchi, M., et al., 1995). As a result, prognosis of adenocarcinoma measuring less than 2 cm in size is very good (Noguchi, M., et al., 1995; Kodama, K., et al., 2001): the 5-year survival rate in the present study was 91 percent. Therefore, the patients of this group should be excluded from any postoperative adjuvant trials in the future if a poor prognosis subgroup cannot be identified. In contrast, patients with a tumor size ranging from 2 to 3 cm tended to show an improved survival by UFT treatment while those with a tumor size of over 3 cm who received UFT treatment had a definitive beneficial effect on survival. These findings indicate that the effect of UFT may be related with some biological malignant factors. Tanaka et al. (Tanaka, F., et al., 2001) reported that patients with non-small cell lung cancer with a high apoptotic index and no p53 aberrant expression who underwent postoperative chemotherapy with UFT demonstrated good prognosis in a retrospective study.

Patient compliance in postoperative adjuvant trials is always a problem. In the trials using cisplatin-based chemotherapy, which was planned to be administered in three or four cycles after operation, only 50 to 70 percent of the planned treatment has been reported to be successfully performed. (Feld, R., et al., 1993; Ohta, M., et al., 1993; Ichinose, Y., et al., 2001; Scagliotti, G. V., et al., 2003) In the present trial, UFT was planned to be given daily for two years. However, only 61 percent of candidate patients completed the two-year treatment in spite of mild toxicities. In fact, the main reasons for discontinuing UFT administration were adverse reactions and patient refusal. Those findings indicate that the compliance of adjuvant chemotherapy trials may not be related to the severity of adverse events induced by chemotherapy. However, if the effect of adjuvant chemotherapy is proven, it is clear that a treatment with mild toxicity has better compliance than a treatment with severe toxicity.

The main difference between cisplatin-based adjuvant chemotherapy trials and UFT adjuvant trials is the duration of the treatment. The former trials have three or four cycles (9 to 16 weeks) (Feld, R., et al., 1993; Ohta, M., et al., 1993; Ichinose, Y., et al., 2001; Scagliotti, G. V., et al., 2003) whereas UFT has been administered daily for 1 or 2 years in the latter trials. (Wada, H., et al., 1996; Tanaka, F., et al., 2001; Tada, H., et al., 2002; Endo, C., et al., 2003; Imaizumi, M., et al., 2003). 5-fluorouracil is well known to not be a dose-dependent agent, but to be a time-dependent agent. Therefore, the daily administration of UFT is an effective method for maintaining the 5-fluorouracil concentration in the blood. In addition, UFT and its metabolites have both been recently reported to have an inhibitory effect on tumor angiogenesis. (Yonekura, K., et al., 1999). If this effect is truly present in the human body, then the daily and long-term administration of UFT may be an even more ideal administration method.

So far, six randomized trials (Wada, H., et al., 1996; Tanaka, F., et al., 2001; Tada, H., et al., 2002; Endo, C., et al., 2003; Imaizumi, M., et al., 2003), including the present trial, comparing surgery alone with postoperative adjuvant treatment with UFT, have been conducted. Among them, three trials demonstrated a survival benefit of UFT. (Wada, H., et al., 1996; Tada, H., et al., 2002). In addition, the results of a meta-analysis of those six trials demonstrated that adjuvant chemotherapy with UFT improved the overall survival (hazard ratio=0.77, 95 percent confidence interval=0.63 to 0.94 percent; P=0.01). (Hamada, C., et al., 2003). Whether the patients with stage II or III have a survival benefit from UFT treatment or whether the 1-year treatment is equivalent to 2-year treatment remains unclear. Nonetheless, based on the results of the present study, patients with completely resected stage I disease, especially T2N0 adenocarcinoma, should benefit from long term, postoperative adjuvant chemotherapy with UFT for a period of 2 or more years.

The present invention is further illustrated by the following example which is not intended to be limiting.

EXAMPLE 1

Patients who had undergone a complete resection of a pathologically documented stage I (T1–2, N0, M0) (Mountain, C. F., et al., 1986) adenocarcinoma were eligible for treatment in accordance with the present invention. Visceral pleural involvement was classified according to the rules of the Japan Lung Cancer Society (Japan Lung Cancer Society, 1987) and either a tumor that was larger than 3 cm or a tumor with any size that was exposed on the visceral pleural surface was classified as T2 tumor. Patients were assigned to either a treatment or control group.

In the treatment group (n=491), UFT (tegafur 250 mg per square meter of body-surface area) in the form of a 100-mg capsule (100 mg tegafur and 224 mg uracil) was given orally in two separate doses, before meals, daily for two years, starting four weeks after operation. The dose was rounded up or down to the nearest 100 mg. Most patients received UFT as two capsules (tegafur 200 mg and uracil 448 mg) bis in die. On each visit at the outpatient clinic, the physician in charge asked all patients whether they regularly took UFT capsules as ordered.

Patients assigned to the control group (n=488) were observed with no further treatment after operation.

The toxicity resulting from UFT administration was graded according to the criteria of the Japan Society of Clinical Oncology, which consist of the World Health Organization criteria with minor modifications. (World Health Organization, 1979). If a grade 2 adverse reaction occurred, the dose of UFT was reduced to 200 mg per square meter. If a grade 3 or greater adverse reaction, a leukocyte count of less than 3,000 per cubic millimeter, a platelet count of less than 70,000 per cubic millimeter, a hemoglobin level of less than 9.5 g per deciliter or aspartate aminotransferase and alanine aminotransferase levels that were more than three times the upper limit of the normal range occurred, then the administration of UFT was suspended.

A follow-up examination was performed every three months for the two years after the patients operation and every six months thereafter. The examination included a physical examination, a complete blood count, blood chemistry work-up, serum tumor marker screening, and chest radiography. A computed tomographic (CT) scan of the thorax and brain, and either a CT scan or an echogram of the upper abdomen were performed every six months for the first two years after the patient's operation and at least twice during the subsequent three years. Any newly appearing lesion suspected of either being recurrence or a second primary cancer was investigated by a biopsy whenever possible. A final diagnosis of such lesions as either recurrence or a second primary cancer was made by the physician in charge.

The primary end point was the overall survival, while the secondary end points were cancer-free survival and safety assessment. The subjects included in the analysis of overall survival and cancer-free survival were all eligible patients. The subjects in the safety assessment consisted of patients who were given UFT.

The sample size was calculated by the method of Schoenfeld and Richter (Schoenfeld, D. A., et al., 1982) under the following conditions: a 5-year survival rate of 70 percent for the non-treatment control group, a hazard ratio of 0.667 for death in the UFT group, the 2-year accrual period, the 5-year follow-up, a significance level for a one-sided test of 0.05, and a statistical power of 80 percent. Since the above calculations resulted in a sample size of 518 patients, the sample size was determined to be 600, with an allowance of about 15 percent for ineligible cases or cases which were lost to follow-up. In May 1995, the sample size was expanded to 984 patients, because it became clear that the 5-year survival rate for those in the control group was better than expected. The newly adopted survival rate was 83 percent, and the accrual period was extended to 3 years. Committee for Efficacy and Safety provided independent monitoring of the study. Haybittle-Peto horizontal boundaries, (Haybittle, J. L., 1971) with a criterion of P<0.001, were used in the interim analyses conducted to determine whether the study should be terminated early.

The overall survival was defined as the time from operation until death from any cause, and the cancer-free survival was defined as the time from operation until the appearance of either the first recurrence of cancer, a second cancer or death from any cause. Survival was estimated by the Kaplan-Meier method, and any differences in survival were computed using the stratified log-rank test. Multivariable analyses using the Cox proportional hazard model were used to estimate the simultaneous effects of prognostic factors on survival. (Cox, D. R., 1972). The interactions with prognostic factors were examined with the Cox proportional hazard model. The SAS statistical software package was used for all calculations. The data were considered to be statistically significant when the P value was 0.05 or less. All statistical tests were two-sided.

The median follow-up for surviving patients was 73 months. The overall survival between the two groups showed a statistically significant difference in favor of the UFT group based on a Kaplan-Meier analysis (P=0.04) by the stratified logrank test. Grade 3 toxicity based on UFT administration was observed in only 10 (2 percent) of 482 patients.

The publications and other materials cited herein to illuminate the background of the invention and to provide additional details respecting the practice of the invention are incorporated herein by reference to the same extent as if they were individually indicated to be incorporated by reference.

While the invention has been disclosed by reference to the details of preferred embodiments of the invention, it is to be understood that the disclosure is intended in an illustrative rather than a limiting sense, as it is contemplated that modifications will readily occur to those skilled in the art, within the spirit of the invention.

REFERENCES

1. Fujii, S., et al., "Effect of coadministration of uracil or cytosine on the anti-tumor activity of clinical doses of 1-(2-tertahydrofuryl)-5-fluorouracil and level of 5-fluorouracil in rodents," *Gann* 70:209–14, 1979.
2. Ikenaka, K., et al., "Effect of uracil on metabolism of 5-fluorouracil in vitro," *Gann* 70:353–9, 1979.
3. Ho, D. H., et al., "Comparison of 5-fluorouracil pharmacokinetics in patients receiving continuous 5-flourouracil infusion and oral uracil plus N1-(2'-Tertahydrofuryl)-5-flourouracil," *Clin. Cancer Res.* 4:2085–8, 1998.
4. Shimizu, E., et al., "A phase II study of UFT in non-small cell lug cancer," *Jpn. J. Cancer Chemother.* 13:2970–3, 1986.
5. Keicho, N., et al., "Phase II study of UFT in patients with advanced non-small cell lung cancer," *Jpn. J. Clin. Oncol.* 16:143–6, 1986.
6. Ichonose, Y., et al., "A phase II trial of oral UFT and cisplatin in inoperable non-small cell lung cancer," *Cancer* 75:2677–80, 1995.
7. Ichinose, Y., et al., "UFT plus cisplatin combination chemotherapy in the treatment of patients with advanced non-small cell lung carcinoma," *Cancer* 88:318–23, 2000.
8. Saito, J., et al., "A phase II trial of oral UFT plus cisplation (CDDP) in patients with non-small cell lung cancer (NSCLC)," *Lung Cancer* 31:285–93, 2001.
9. Ichinose, Y., et al., "UFT plus cisplatin with concurrent radiotherapy for locally advanced non-small-cell long cancer: a multiinstitutional phase II trial," *Prog. Proc. Am. Soc. Clin. Oncol.* 21:321a (Abstract), 2002 and Ichinose, Y., et al., "Uracil/Tegafur Plus Cisplatin with Concurrent Radiotherapy for Locally Advanced Non-small-Cell Lung Cancer: A Multi-institutional Phase II Trial, "Clin. Cancer Res. 10:4369–73, 2004
10. Ichinose, Y., et al., "A phase II trial UFT plus cisplatin with concurrent radiotherapy for locally advanced non-small-cell lung cancer," *Oncology* 13(3):98–101, 1999.
11. Schiller, J. H., et al., "Comparison of four chemotherapy regimens for advanced non-small cell lung cancer," *N. Engl. J. Med.* 346:92–8, 2002.
12. Vokes, E. E., et al., Randomized phase II study of cisplatin with gemcitabine or paclitaxel or vinorelbine as induction chemotherapy followed by concomitant chemoradiotherapy for stage IIIB non-small-cell lung cancer: cancer and leukemia group B study 9431," *J. Clin. Oncol.* 20:4191–8, 2002.
13. Wada, H., et al., "Adjuvant chemotherapy after complete resection in non-small-cell lung cancer," *J. Clin. Oncol.* 14:1048–54, 1996.
14. Okimoto, N., et al., "A randomized controlled postoperative adjuvant chemotherapy trial of CDDP+VDS+UFT and UFT alone in comparison with operation only for non-small cell lung carcinomas (Second Study)," *Jpn. J. Lung Cancer* 36:863–71, 1996.
15. Mountain, C. F., "A new international staging system for lung cancer," *Chest.* 89(4):225s–33s, 1986.
16. *WHO Handbook for Reporting Results for Cancer Treatment*, Geneva: World Health Organization Offset Publication No. 48, 14–21, 1979.
17. Shirakusa, T., et al., "Lung cancer in Japan: Analysis of lung cancer registry for resected cases in 1994," *Jpn. J. Lung Cancer* 42:555–66, 2002.
18. Breathnach, O. S., et al., "Bronchioloalveolar carcinoma of the lung: recurrences and survival in patients with stage I disease," *J. Thorac. Cardiovasc. Surg.* 121:42–7, 2001.
19. Myrdal, G., et al., Survival in primary lung cancer potentially cured by operation: influence of tumor stage and clinical characteristics," *Ann. Thorac. Surg.* 75:356–63, 2003.
20. Noguchi, M., et al., "Small adenocarcinoma of the lung: histologic characteristics and prognosis," *Cancer* 75:2844–52, 1995.
21. Kodama, K., et al., "Prognostic value of ground-glass opacity found in small lung adenocarcinoma on high-resolution CT scanning," *Lung Cancer* 33:17–25, 2001.

22. Tanaka, F., et al., "Apoptosis and p53 status predict the efficacy of postoperative administration of UFT in non-small cell lung cancer," Br. J. Cancer 84:263–9, 2001.
23. Feld, R., et al., "Adjuvant chemotherapy with cyclophosphamide, doxorubicin, and cisplatin in patients with completely resected stage I non-small-cell lung cancer," J. Natl. Cancer Inst. 85:299–306, 1993.
24. Ohta, M., et al., "Adjuvant chemotherapy for completely resected stage III non-small-cell lung cancer," J. Thorac. Cardiovasc. Surg. 106:703–8, 1993.
25. Ichinose, Y., et al., "A Randomized Phase III Trial of Postoperative Adjuvant Chemotherapy in Patients with Completely Resected Stage IIIa-N2 Non-Small Cell Lung Cancer: Japan Clinical Oncology Group (JCOG9304) Trial," Prog. Proc. Am. Soc. Clin. Oncol. 20:311a (Abstract), 2001.
26. Scagliotti, G. V., et al., "Randomized study of adjuvant chemotherapy for completely resected stage I, II, or IIIA non-small-cell lung cancer," J. Natl. Cancer Inst. 95:1453–1461, 2003.
27. Tanaka, F., et al., "Postoperative oral administration of UFT for completely resected pathologic stage I non-small cell lung cancer: the West Japan Study Group for Lung Cancer Surgery (WJSG), the 4th Study," Prog. Proc. Eur. Cancer Conference 37:S29 (Abstract), 2001.
28. Tada, H., et al., "Randomized Study of Adjuvant Chemotherapy for Completely Resected Non-Small Cell Lung Cancer," Prog. Proc. Am. Soc. Clin. Oncol. 21:313a (Abstract), 2002.
29. Endo, C., et al., "A randomized trial of postoperative UFT therapy in p stage I, II non-small cell lung cancer: North-East Japan Study Group for Lung Cancer Surgery," Lung Cancer 40:181–6, 2003.
30. Imaizumi, M., et al., "A randomized trial of postoperative adjuvant chemotherapy for p-stage I non-small cell lung cancer (4th cooperative study)," Prog. Proc. World Conference 41:S54 (Abstract), 2003.
31. Yonekura, K., et al., UFT and its metabolites inhibit the angiogenesis induced by murine renal cell carcinoma, as determined by a dorsal air sac assay in mice," Clin. Cancer Res. 5:2185–91, 1999.
32. Hamada, C., et al., "Efficacy or oral UFT for adjuvant chemotherapy after complete resection of non-small cell lung cancer: Meta-analysis of six randomized trials in 2003 patients," Prog. Proc. Euro. Cancer Conference 39:S231 (Abstract), 2003.
33. Mountain, C. F., "Revisions in the International System for Staging Lung Cancer," Chest 111 (6):1710–17, 1997.
34. Mountain, C. F., et al., "Regional Lymph Node Classification for Lung Cancer Staging," Chest 111 (6):1718–1723, 1997.
35. The Japan Lung Cancer Society, General Rule for Clinical and Pathological Record of Lung Cancer, 3rd Ed. Tokyo: Kanehara, 1987.
36. Schoenfeld, D. A., et al., "Nomograms for calculating the number of patients needed for a clinical trial with survival as an endpoint," Biometrics 38:163–170, 1982.
37. Haybittle, J. L., "Repeated assessment of results in clinical trials of cancer treatment," Br. J. Radiol. 44:793–797, 1971.
38. Cox, D. R., "Regression models and life-tables," J. Roy Statist. Soc. Ser. B. 34:187–220, 1972.
39. Kato, H., et al., "A randomized phase III trial of adjuvant chemotherapy with UFT for completely resected pathological stage I (T1N0M0, T2N0M0) adenocarcinoma of the lung," Proc. Am. Soc. Clin. Oncol. 22:621, 2003 (Abstract 2498).

TABLE 1

Patient Characteristics

| Characteristics | Control (N = 488) | UFT (N0 = 491) |
|---|---|---|
| Age (yr) | | |
| Mean (range) | 62 (45–75) | 62 (45–75) |
| <65 | 275 | 274 |
| >65 | 213 | 217 |
| Female sex (no. of patients) | 249 | 253 |
| ECOG performance status (no. of patients) | | |
| 0 | 369 | 376 |
| 1 | 113 | 105 |
| 2 | 6 | 10 |
| Pathological T status (no. of patients) | | |
| 1 | 354 | 362 |
| 2 | 134 | 129 |
| Pleural invasion (no. of patients)* | | |
| 0 | 346 | 340 |
| 1 | 114 | 120 |
| 2 | 28 | 29 |
| Unknown | 0 | 2 |
| Tumor size (no. of patients) | | |
| <=2 cm | 204 | 208 |
| 2 to 3 cm | 170 | 174 |
| >3 cm | 114 | 109 |
| Location of the tumor (no. of patients) | | |
| Rt. upper lobe | 189 | 182 |
| Rt. middle lobe | 34 | 41 |
| Rt. lower lobe | 87 | 102 |
| Rt. Lobes | 2 | 2 |
| Lt. upper lobe | 114 | 107 |
| Lt. lower lobe | 60 | 54 |
| Lt. lobes | 2 | 3 |
| Operation modality (no. of patients) | | |
| Lobectomy | 487 | 490 |
| Pneumonectomy | 1 | 1 |

*0 = a tumor with no pleural involvement or a tumor that reaches the visceral pleura but does not extend beyond the elastic layer; 1 = a tumor that extends beyond the elastic layer of the visceral pleura but is not exposed on the pleural surface; 2 = a tumor that is exposed on the pleural surface but does not involve the parietal pleura.

TABLE 2

UFT-Related Adverse Reaction

| Toxicity (n = 482), percent of patients | Grade | | | |
|---|---|---|---|---|
| | 1 | 2 | 3 | 4 |
| Leukopenia | 2 | 1 | 0 | 0 |
| Thrombocytopenia | <1 | 0 | 0 | 0 |
| Hemoglobin | <1 | <1 | 0 | 0 |
| Bilirubin | 1 | <1 | 0 | 0 |
| GOT | 6 | 2 | <1 | 0 |
| GPT | 6 | 2 | 0 | 0 |
| ALP | 2 | <1 | 0 | 0 |
| Anorexia | 9 | 8 | 1 | — |
| Nausea/Vomiting | 10 | 3 | 1 | — |
| Diarrhea | 2 | 1 | <1 | 0 |
| Alopecia | <1 | 0 | 0 | — |

TABLE 3

| Pattern | Control (n = 488) | UFT (n = 491) |
|---|---|---|
| Intrathoracic only | | |
| Local recurrence | 8 | 17 |
| Pulmonary metastases | 38 | 36 |
| Local recurrence plus Pulmonary metastases | 12 | 3 |
| Second Cancer | 11 | 11 |
| Extrathoracic only | | |
| Recurrence | 33 | 23 |
| Second cancer | 18 | 14 |
| Intrathoracic plus | | |
| Extrathoracic recurrence | 9 | 7 |
| Total No. (percent of all patients) | 129 (26.4) | 111 (22.6) |

What is claimed is:

1. A method for treating lung cancer by postoperative adjuvant chemotherapy with UFT which comprises orally administering about 100 to about 500 mg/m$^2$/day UFT to a postoperative lung cancer patient in need thereof for a period of at least about two years, wherein the patient has a primary tumor which is classified as T2 according to the TNM classification, and wherein the patient has pathological stage IB adenocarcinoma of the lung or a primary tumor of a size more than 3 cm.

2. The method of claim 1, wherein the adenocarcinoma is completely resected prior to treatment.

3. The method of claim 1, wherein the UFT is administered in an amount of 200 to 300 mg/m$^2$/day.

4. The method of claim 1, wherein the UFT is administered in an amount of 250 mg/m$^2$/day.

* * * * *